United States Patent [19]
Hamilton et al.

[11] Patent Number: 5,281,232
[45] Date of Patent: Jan. 25, 1994

[54] REFERENCE FRAME FOR STEREOTACTIC RADIOSURGERY USING SKELETAL FIXATION

[75] Inventors: Allan J. Hamilton; Bruce A. Lulu, both of Tucson, Ariz.

[73] Assignee: Board of Regents of the University of Arizona/ University of Arizona, Tucson, Ariz.

[21] Appl. No.: 959,819

[22] Filed: Oct. 13, 1992

[51] Int. Cl.$^5$ .............................................. A61B 6/04
[52] U.S. Cl. ................................ 606/130; 128/653.5
[58] Field of Search ................ 606/130, 88; 604/116; 128/653.1, 653.2, 653.5, 20; 378/180; 5/428, 425, 625

[56] References Cited

U.S. PATENT DOCUMENTS

| | | | |
|---|---|---|---|
| 4,583,538 | 4/1986 | Onik et al. | 606/130 |
| 4,682,810 | 7/1987 | Zarka | 5/625 |
| 4,916,725 | 4/1990 | Quinter et al. | 5/428 |
| 4,926,849 | 5/1990 | Downey | 128/20 |

Primary Examiner—Stephen C. Pellegrino
Assistant Examiner—Tamara L. Graysay
Attorney, Agent, or Firm—Antonio R. Durando; Harry M. Weiss

[57] ABSTRACT

A body-support frame comprising a horizontal table having two adjustable braces that can be moved along the main axis of the table for straddling a patient lying within the frame. Each brace is equipped with a swiveled clamp attached to an adjustable system of bracket-arms for the skeletal fixation and immobilization of the patient craniad and caudad to the area of interest. The frame contains orthogonal scales for orthogonal localization and measurements of the area of interest with reference to a chosen set of coordinates within the table. The frame also contains three adjustable radiographic calibration targets that are used for selectively setting a plane of reference in the proximity of the area of interest, so that the plane may be used for lining up the frame with radiographic imaging and radiation treatment apparatus. An additional, adjustable radiographic target may be provided for fine calibration of the position of the reference coordinates by permitting its placement as near as possible to the area of interest externally to the body of the patient. The apparatus is used to determine the exact coordinates of the area of interest with reference to the chosen reference point while the body of the patient is immobilized. These coordinates are then translated to an exact position in the radiation therapy apparatus for subsequent stereotactic radiosurgery.

27 Claims, 5 Drawing Sheets (PRIOR ART)

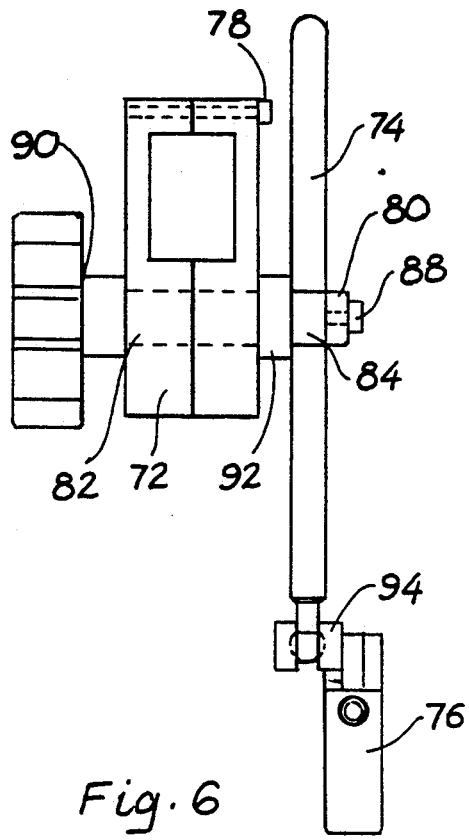
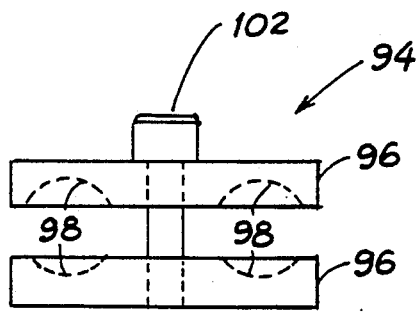
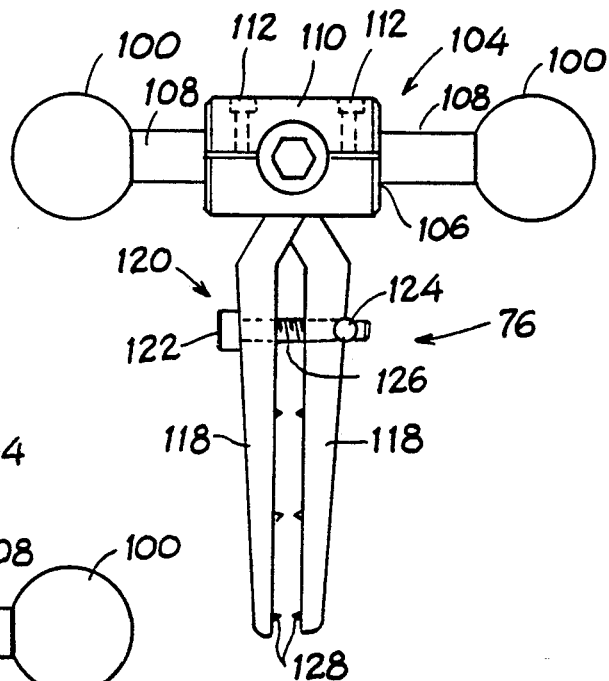
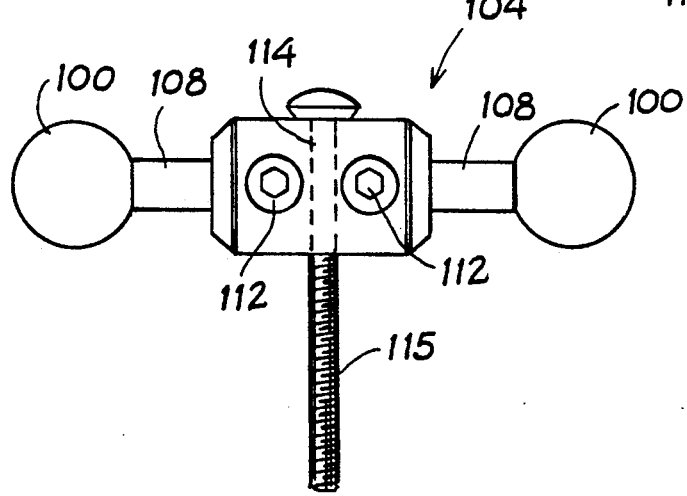
Fig. 6
Fig. 7
Fig. 8a
Fig. 8b

REFERENCE FRAME FOR STEREOTACTIC RADIOSURGERY USING SKELETAL FIXATION

BACKGROUND OF THE INVENTION

1. Field of the Invention

This invention is related in general to the fields of stereotactic radiosurgery and radiation therapy. In particular, the invention provides a new method and apparatus for producing a precise set of coordinates of the portion of a patient's body affected by a tumor with reference to a fixed frame wherein the patient is immobilized, so that the required dosage of radiation can be accurately delivered to the prescribed target volume with substantial sparing of surrounding normal tissues.

2. Description of the Related Art

The main object of radiotherapy is to deliver the prescribed dose of radiation to a tumor in a patient while minimizing the damage to surrounding, healthy, tissue. Since very-high-dose radiation (in the order of several thousand rads or cGy, typically generated by a linear accelerator) is normally used to destroy tumors in radiotherapy, the high dose is also destructive to the normal tissue surrounding the tumor. Therefore, it is essential that the delivery of radiation be limited precisely to the prescribed target volume (i.e., the tumor plus adequate margins). This is normally accomplished by placing appropriately constructed shielding blocks in the path of the radiation beam. Thus, the goal is to accurately identify the malignancy within the body of the patient and to target the prescribed dosage of radiation to the desired region in the immobilized patient.

To that end, the ideal procedure requires the identification of the exact anatomical location of the tumor and the corresponding accurate positioning of the radiation field during treatment. This could be easily achieved if it were possible to locate and treat the tumor at the same time. In practice, though, this is not possible because the equipment used to identify the tumor (x-ray machine, computed tomography equipment, or any of the other scanning machines currently in use) is separate from the equipment used for the therapeutic irradiation of the patient, requiring the movement and repositioning of the patient from one piece of equipment to the other.

As illustrated in schematic form in FIG. 1, a conventional treatment unit 10 consists of a linear accelerator (linac) head 2 mounted on a gantry 4 so that its high-energy emissions R irradiate a patient P lying on a table 6 directly below, typically through shielding blocks 8 attached to the head. A bracket 12 supporting a detector 14 may be mounted on the opposite side of the head within the field of radiation in order to take radiographs of the patient being treated. The gantry 4 is movable around a pivot 16 to permit the rotation of the head (and of the detector) around the patient to afford different views of the area to be treated ("multiple fields" treatment).

The normal procedure involves the use of a diagnostic simulator, which is a diagnostic x-ray machine with the same physical characteristics of the radiation therapy machine (schematically also represented by FIG. 1, where a diagnostic x-ray head replaces the linac head 2), so that the field of view of the low-energy x rays emitted in the simulator is the same as that of the high-energy radiation emitted in the radiation therapy machine. Prior to treatment, the patient is radiographed using the simulator and an image of the target area is obtained with low-energy radiation, which yields good image quality. The exact target volume is then delineated on the radiograph by a physician and matching shielding blocks are constructed to limit the field of view of the irradiating machine to the region so delineated.

A different approach has been used in the field of cranial radiosurgery, which requires very precise high-intensity radiation delivered in a single session. Rather than irradiating the target through shielding blocks, which provide only a coarse alignment of the tumor area with the field of emission, cranial radiosurgery relies on a highly focussed stereotactic radiation beam pointed precisely toward the center of the tumor. In order to be able to direct the radiation with sufficient accuracy, a cranial frame consisting of a rigid ring is affixed to the skull of a patient below the tumor area by means of at least four pressure pins evenly distributed around the ring. The pins compress the bone to the point of becoming rigidly affixed to the skull, thus providing a fixed frame of reference for delineating the position of the malignancy. With the use of scanning equipment, such as a CT scanner, the exact location of the tumor can thus be mapped in terms of three-dimensional coordinates in relation to the ring of the cranial frame. Once these exact coordinates are known, the patient is moved to the linac machine where the cranial frame is lined up with a special cranial support calibrated to the machine's own reference system and the frame is positioned so that the stereotactic radiation beam is focussed on the center of the tumor. Thus, as the linac's gantry rotates around head of the patient for multiple-fields treatment, the tumor is subjected to the cumulative amount of radiation emitted during the radiation session, while the areas surrounding the tumor receive only the radiation emitted while the path of the beam passed through them.

This technique requires precise measurements and targeting of the radiation beam, but it is indispensable for the treatment of cranial tumors, where even a slight misalignment of the radiation beam may cause severe damage to surrounding vital tissue. Therefore, it would be very desirable to have an apparatus that permitted the use of a similar technique for extracranial applications. The present application is directed at the development of a device that enables the use of this technique for stereotactic localization and radiation therapy of extracranial targets.

BRIEF SUMMARY OF THE INVENTION

One objective of this invention is the development of an apparatus that permits the immobilization of a patient's body for conducting stereotactic localization of a target tumor during the scanning procedure.

Another objective is an apparatus that can also be used as a reference frame for targeting the radiation beam and for conducting radiosurgery of extracranial targets in a linear accelerator after the scanning procedure.

A further goal of the invention is an apparatus that permits the focussing of the radiation beam on the target tumor with a degree of precision that is acceptable within the tolerances allowed for high-dose radiosurgery.

Still another objective of the invention is an apparatus that can be used as an accessory to existing radiation-therapy diagnostic and treatment units.

A final objective of this invention is the realization of the above mentioned goals in an economical and commercially viable manner. This is done by utilizing components and methods of manufacture that are either already available in the open market or can be developed at competitive prices.

According to these and other objectives, the present invention consists of a body-support frame comprising a horizontal table having two adjustable braces that can be moved along the main axis of the table for straddling a patient lying within the frame. Each brace is equipped with a swiveled clamp attached to an adjustable system of bracket-arms for the skeletal fixation and immobilization of the patient craniad and caudad to the area of interest. The frame contains orthogonal scales for orthogonal localization and measurements of the area of interest with reference to a chosen set of coordinates within the table. The frame also contains three adjustable radiographic calibration targets that are used for selectively setting a plane of reference in the proximity of the area of interest, so that the plane may be used for lining up the frame with radiographic imaging and radiation treatment apparatus. An additional, adjustable radiographic target may be provided for fine calibration of the position of the reference coordinates by permitting its placement as near as possible to the area of interest externally to the body of the patient. The apparatus is used to determine the exact coordinates of the area of interest with reference to the chosen reference point while the body of the patient is immobilized. These coordinates are then translated to an exact position in the radiation therapy apparatus for subsequent stereotactic radiosurgery.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIG. 6 is an elevational front view of the preferred embodiment of the vise, arm and clamp of the invention, as seen from the left side of FIG. 5.

FIG. 7 is an isolated elevational view of the double-swivel joint used to connect the straight arm with the clamp frame of the invention.

FIG. 8a is an elevational view of the fixation clamp frame of the invention.

FIG. 8b is an elevational view of a cancellous screw mounted on the fixation clamp frame of the invention.

DESCRIPTION OF THE PREFERRED EMBODIMENT OF THE INVENTION

This invention is directed at developing an apparatus for the skeletal fixation of a patient to a rigid frame to permit the stereotactic localization and radiation therapy of extracranial targets, such as targets in the thoracic cavity, abdominal cavity, upper and lower extremities, and paraspinal regions. The device of the invention also permits the determination of an orthogonal set of coordinates for the target and the translation of these coordinates from computerized tomography or equivalent scans to the linear accelerator.

Figure 1:
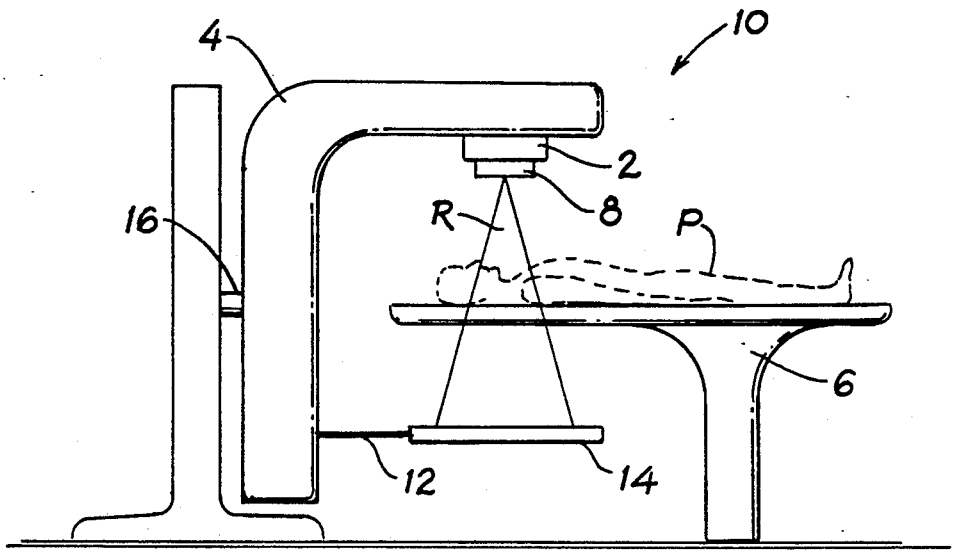
FIG. 1 is an elevational schematic representation of a typical radiation therapy unit.

Referring to the drawings, wherein like parts are identified with like symbols and numerals throughout this specification, FIG. 1 illustrates in schematic elevational representation a typical linear accelerator (linac) radiation therapy unit. Although the present invention can be used in equivalent fashion with other radiation therapy equipment, the linac machine will be referred to consistently herein for illustration. The critical feature of any radiation unit that is relevant for this disclosure is a calibration system that permits the positioning of a chosen target exactly within the focal point of the radiation beam.

Figure 2:
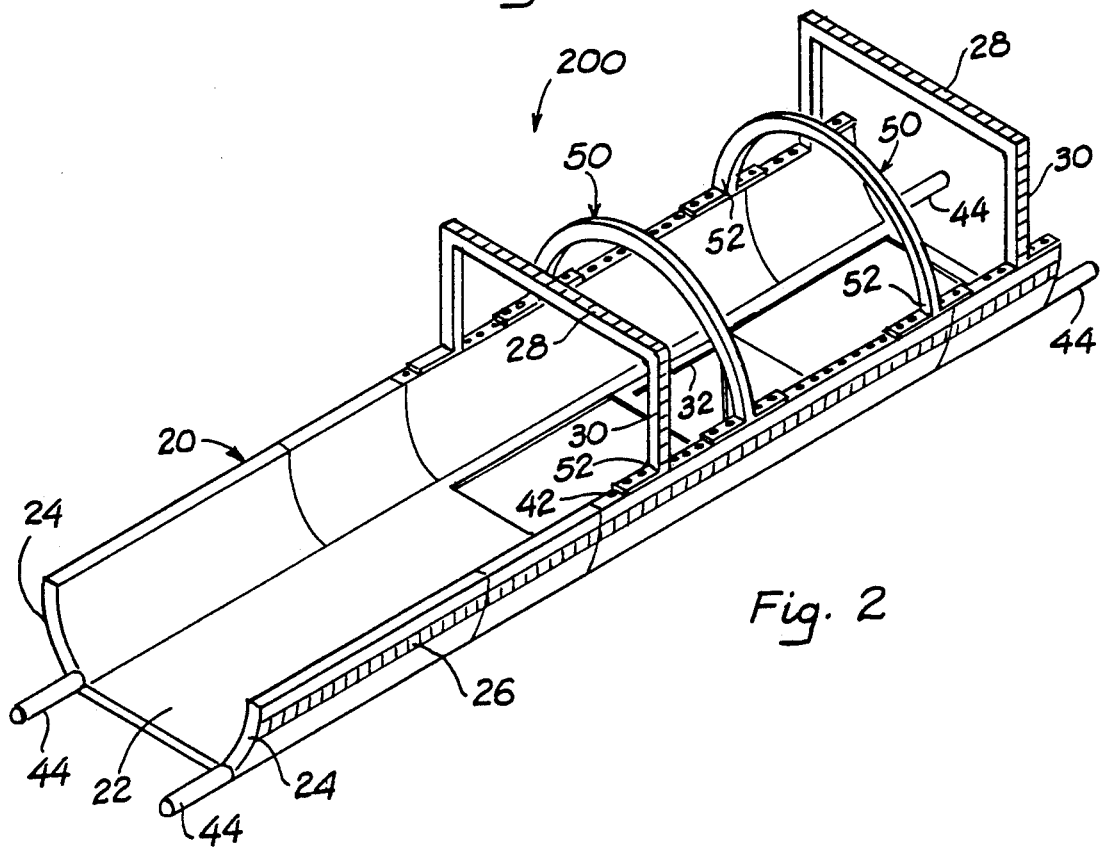
FIG. 2 is a perspective view of a body-support frame for the skeletal fixation of a patient according to the present invention.
Figure 3:
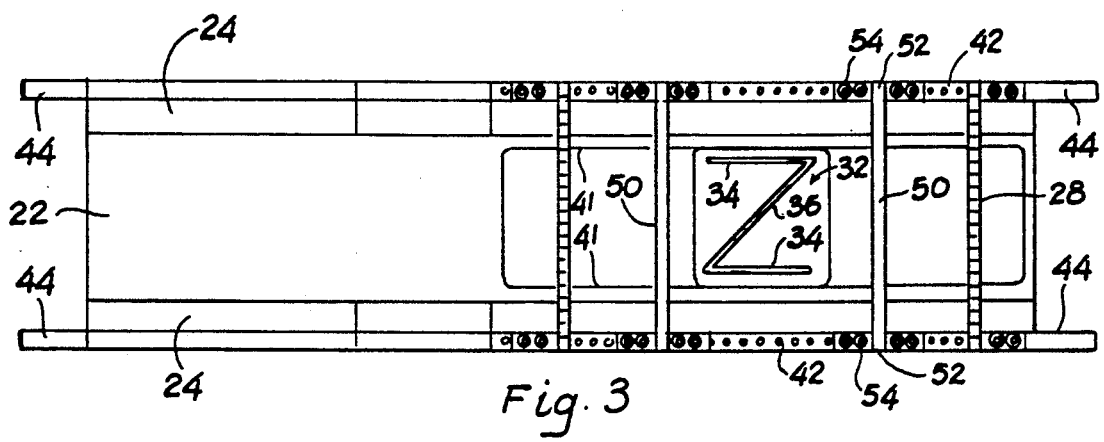
FIG. 3 is a top view of the table illustrating an N-shaped reference sight mounted within the retaining side-walls of the invention.
Figure 4:
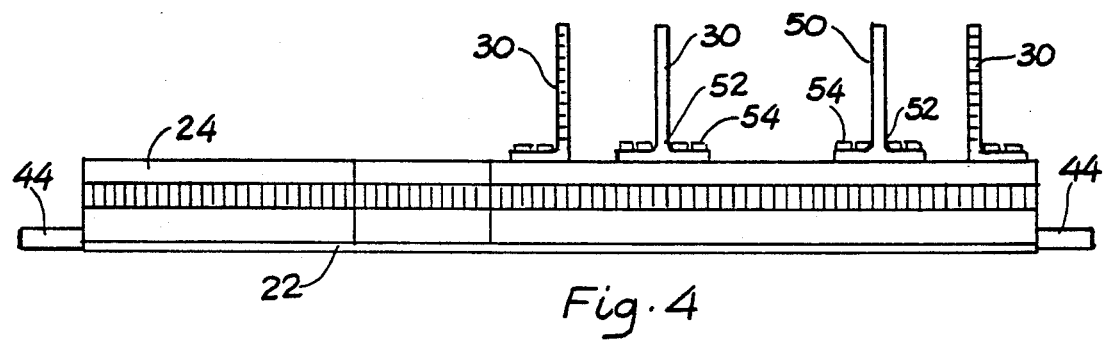
FIG. 4 is a front elevational view of the table illustrating the removable portions of the side-walls and the x- and z-coordinate scales mounted on the frame of the invention.

FIGS. 2-4 illustrate the body-support frame 200 of the invention, comprising a horizontal table 20 for supporting the body of a patient and at least two braces 50 straddled across the table. The table 20 consists of a flat horizontal platform 22 sufficiently long and wide to receive the body of a human patient lying on it, either in supine or prone position, and of two retaining side-walls 24 rigidly attached to the platform or integral thereto, so as to form a structure functionally equivalent to a conventional stretcher or gurney. As in the case of stretchers, sets of handles 44 are provided at both sides of the platform 22 to permit the transportation of the patient held on the table. Differently from conventional stretchers, though, the table 20 must be constructed with rigid material in order to minimize physical deformations caused by mechanical and thermal stresses that would alter the coordinates of a chosen target in the body of the patient held immobilized on the table. The overall cross-sectional size of the table 20, including the braces 50, must not exceed the space available for positioning the frame in the scanning machine. In the case of a typical CAT scanner, the bore of the machine is round and approximately 28 inches in diameter. Accordingly, the geometry of the side-walls 24 and of the braces 50 may be selected with a conforming shape in order to maximize space utilization, as shown in the figures.

Three measurement scales are affixed to the table 20 in positions corresponding to a chosen system of coordinates. The scales shown in the figures correspond to an orthogonal x,y,z coordinate system, but any system that allows the exact determination of the location of a point with respect to a reference point on the frame 200 can be used in equivalent manner, as would be obvious to those skilled in the art. Thus, an x-axis scale 26 is affixed rigidly to each side-wall 24 in parallel to the longitudinal axis of the table 20; a y-axis scale 28 is affixed rigidly to the side-walls 24 perpendicularly to the longitudinal axis of the table 20; and a z-axis scale 30 is similarly affixed rigidly to the table (or, equivalently, to any other part of the structure capable of supporting the scale) perpendicularly to the plane containing the platform 22. Obviously, these scales provide the means for setting the origin of an orthogonal coordinate system that can be used to establish the corresponding coordinates of an identified target, such as a tumor in a patient, positioned within the table 20. Once these coordinates are measured, so long as the target does not move with respect to the table, the position of the target can be reestablished simply by measuring its coordinates from the origin of the orthogonal system. Thus, if the position of a tumor in the body of a patient immobilized within the frame 200 is identified, that position can be measured and expressed in terms of coordinates relative to the orthogonal system provided by the measurement scales 26, 28 and 30.

As will become more apparent from the description given below of the operation of the apparatus of the invention, an N-shaped reference sight 32 is provided on the surface of the platform 22 for radiographic confirmation of the exact position of scanner images taken along the longitudinal axis of the table 20. Referring to the top view of the table seen in FIG. 3, the sight 32 consists of three straight segments of material, such as aluminum, that is visible in radiographic scanning images without producing significant artifacts. The two segments 34 corresponding to the parallel legs of the N-shaped sight are placed precisely in parallel to the main (longitudinal) axis of the platform 22, preferably near the interior face of the retaining side-walls 24, so that the slanted segment 36 is disposed across the width of the platform in variable x-y coordinates. The sight 32 is attached to a rigid support panel 40, such as a rectangular sheet of plexiglass, that is slidably mounted on supporting longitudinal tracks 41 within the retaining side-walls 24 on the top surface of the platform 22. Thus, the sight can be moved along the x-axis of the table 20 to a position underlying the region of interest in the body of a patient lying on the table (such as the position of a tumor), so as to be visible in radiographic images produced in scanning the tumor region.

Figure 5:
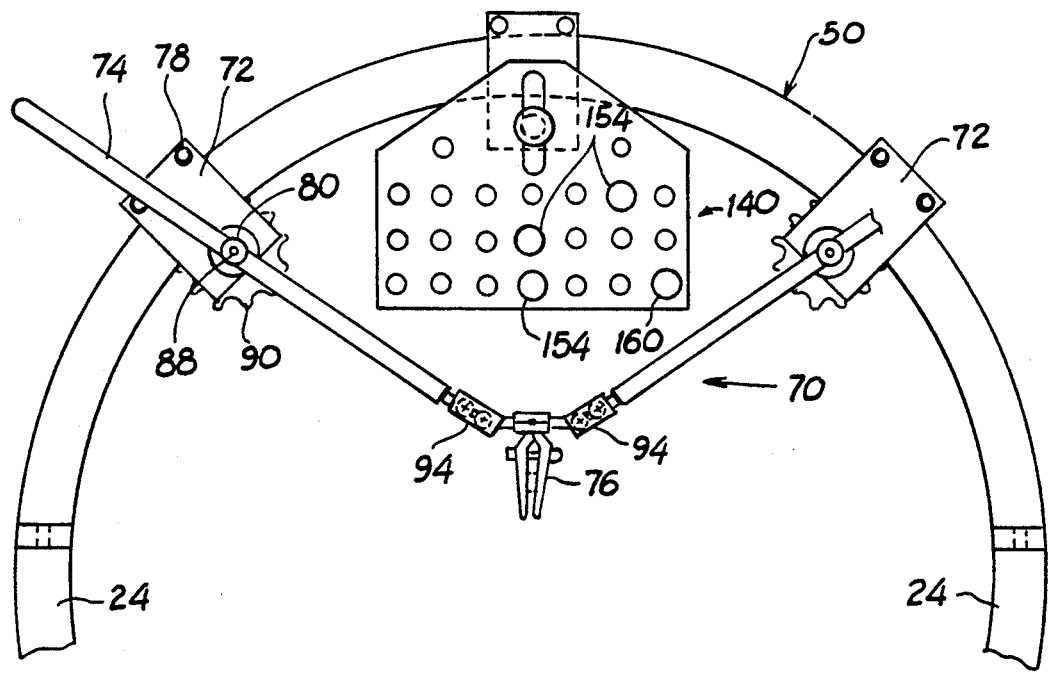
FIG. 5 is an elevational side view of the preferred embodiment of the brace of the invention, illustrating the vise, arm and clamp of the skeletal fixation mechanism attached to each side of the brace.

FIG. 5 shows the detailed geometry of the preferred embodiment of each brace 50 straddling the table of the invention. Each brace consists of a rigid span of solid material sufficiently large to envelop the body of a patient lying in the frame 200. Each brace lies in a plane orthogonal to the longitudinal axis of the table 20 and is adjustably connected to the retaining side-walls 24 so that the position of the brace can be shifted along the x coordinate of the table to lie outside the region of interest in the patient. That is, each brace is moved along the side-walls 24 of the table to a position that permits the fixation of the patient as closely as possible to the region of interest, but that is outside the area that will be evaluated radiographically. Accordingly, the two braces are positioned to straddle the body of the patient craniad and caudad to the area of interest. Since after skeletal fixation a patient is expected to spend many hours in an immobilized position on the table, the side walls 24 may be constructed in removable sections, as illustrated in FIGS. 2-4; that permits the removal of those sections that are not being used to support the braces 50, thus giving the patient some freedom of limb movement.

As seen particularly in FIGS. 2, 3 and 4, each end 52 of a brace 50 is adjustably fastened to the corresponding side-wall 24 by means of removable pins or bolts 54 that are slotted or screwed through the brace and into apposite receiving holes 42 located at exact discrete intervals along the side-walls 24. Thus, the location of each brace can be adjusted along the x coordinate in discrete steps corresponding to the distance between two adjacent holes 42. As will be explained below, finer adjustments for the position of the apparatus supported by each brace are possible by means of swivel joints and spacers built into the brace itself. This apparatus, which is common to each brace 50, consists generally of a skeletal fixation mechanism 70 for immobilizing a patient lying on the table. At least one of the braces also comprises a radiographic calibration device 140 that is used for selectively setting a plane of reference in the proximity of the area of interest. Finally, at least one of the braces is also equipped with an adjustable radiographic target 160 for fine calibration of the position of the reference coordinate system.

The skeletal fixation mechanism 70 mounted on each brace comprises at least one vise 72 slidably fastened to the brace 50, so that its position may be adjusted along the span of the brace. One end of a swivel arm 74 is adjustably connected to the vise 72 by means of an upper swivel joint, while the other end of the arm is connected to a skeletal fixation clamp 76 by means of another, lower swivel joint. Thus, by virtue of the freedom of movement of the vise 72 along the brace 50, of the swivel arm 74 around the upper swivel joint, and of the fixation clamp 76 around the lower swivel joint, the fixation clamp 76 can be oriented to reach any point in the proximity of the brace across the width of platform 22. It is a critical feature of this invention that all movable parts (such as the vise, swivel joints, and clamp) be capable of being rigidly and immovably fixed once a position is chosen for the clamp, as required for a given procedure. Obviously, any mechanical system consisting of fixable, hinged levers that permit the accurate and rigid placement of the fixation clamp 76 over a patient lying under the support brace 50 would be equivalently suitable to practice the invention.

In the preferred embodiment illustrated in the drawings, each brace 50 consists of an arcuated portion spanning over the table 20 with two ends removably attached to the side-walls 24 by means of pins 54. Two vises 72 having opposite sides are slidably mounted on the arcuated portion of the brace 50, so that the position of each can be adjusted to anywhere along the span of the brace. Each vise comprises tightening bolts 78 (at least one) to fasten the vise to the desired position along the brace and, as illustrated in the front view of FIG. 6, a swivel rod 80 rotatably mounted in a longitudinal bore 82 between the two sides of the vise. One end of the rod 80 contains a radial through-hole 84 for receiving in slidable connection a straight swivel arm 74 having a conforming cross-section. Although not critical to the functioning of the invention, as will become apparent from the description given below, a compression screw 88 may be provided on the swivel rod 80 for locking the arm 74 in place after it has been slid to the desired position in the through-hole 84. The other end of the rod 80 contains a tightening knob 90, screwably mounted on the rod, which is used to lock the rod in position by providing a clamping action between the knob and the arm 74 across the vise. A tubular collar 92 may be inserted around the swivel rod 80 as a spacer to adjust the longitudinal position of the arm 74. Obviously, collars with different lengths may be used along the rod 80 on either side of the vise to provide the desired spacing for fine adjustments of the position of the arm 74.

The lower end of each arm 74 is coupled to the skeletal fixation clamp 76 by means of a double-swivel joint 94. In the preferred mode, this joint consists of two facing blocks 96, each containing opposite hemispherical recesses 98 wherein conforming spheres 100 built into the lower end of each arm 74 and in the frame 104 of the clamp are housed, as illustrated in FIGS. 5, 7 and 8a. This configuration obviously permits the rotation of each sphere within the cavity in which it is housed, providing a high degree of freedom in the motion of the clamp. A locking screw 102 that fastens the two blocks 96 together also provides the means for tightening the blocks around the spheres 100 and fixing the clamp 76 in the desired position.

Figure 9:
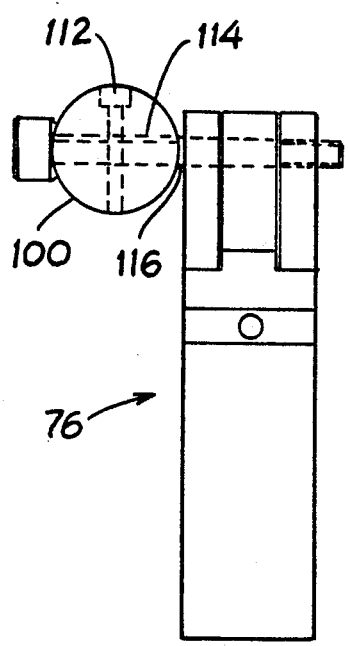
FIG. 9 is a view of the fixation clamp shown in FIG. 8 as seen from the right side of that figure.

FIGS. 8a and 9 show the construction and functional components of the skeletal fixation clamp 76 of the invention. The clamp frame 104 consists of a support housing 106 having two side-arms 108, each comprising a swivel sphere 100 connected to the double-swivel joint 94 at each side of the clamp. The support housing 106 has a removable top 110 that is clamped to the housing by means of retaining screws 112. The main body of the support housing and the removable top contain facing semicircular recesses that define a cylindrical channel 114 disposed radially across the housing, wherein a clamp axle 116 is rotatably mounted to support the clamp 76. As the retaining screws 112 are tightened, the axle 116 is locked in place with respect to the housing, thus also fixing the position of the clamp in relation to the housing.

As better illustrated in FIG. 9, the clamp 76 is rigidly attached to clamp axle 116, so that the clamp's position is fixed when the axle is tightened to the housing 106. As would be obvious to those skilled in the art, different mechanical arrangements could be used to support the fixation clamp 76, the critical feature being that it be capable of multidirectional pivotal adjustment and rigid fixation with respect to the pair of straight swivel arms 74 connecting it to the brace. The clamp 76 consists of two facing jaws 118 that are pulled together by a normally-open spring-loaded compression bolt mechanism 120 that permits a user to adjustably compress, grip and firmly hold a selected part of the anatomy of a patient. In the preferred mode of practicing this invention, the mechanism 120 consists of a threaded bolt 122 passed from one side of the clamp through transverse guide-holes in the jaws 118 and screwably connected to a threaded nut 124 on the other side of the clamp. A spring 126 around the bolt 122 between the two jaws of the clamp ensures that the jaws remain open within the adjustment provided by the compression bolt mechanism. The geometry of the jaws is chosen to conform to the shape of the anatomical part for which they are intended. The shape and size illustrated in the figures (approximately 5 cm long, 1.5 cm wide and 3 to 5 mm thick) have been designed specifically for spinous process attachment, but it has been found to be suitable as well for clamping other skeletal parts. Friction bumps 128 are added on the contact surface of the jaws to increase their gripping of the bone.

The skeletal fixation mechanism of the invention can also be used without the clamp 76, utilizing a cancellous screw instead. As illustrated in FIG. 8b, a cancellous screw 115 of the type normally used for cancellous fixation by orthopedic surgeons can replace the clamp axle 116 in the cylindrical channel 114 of the clamp frame 104. Thus, the screw provides fixation by being driven directly into the bone.

Note that each of the two braces 50 must be equipped with a skeletal fixation mechanism 70 in order to provide the ability to grip two fixation points on the skeleton of a patient. Thus, by choosing a bone in the vicinity of the region of interest (such as the spinal column for the treatment of a chordoma, for instance), the bone can be clamped by the two fixation clamps and immobilized for radiographic imaging and for stereotactic treatment. For example, an incision is made through the tissue above the spinal column and each fixation clamp is positioned around the spinous process of a selected vertebra. The clamps are then closed to firmly grip and immobilize the bone. The patient is now ready for radiographic scanning to locate the precise coordinates of the tumor in relation to the reference system on the table 20. Then, these coordinates can be used to precisely position the table in the linear accelerator machine to focus the radiation beam on the desired region in the body of the patient (corresponding, of course, to the region delineated by the coordinates produced by radiographic scanning).

Figure 10:
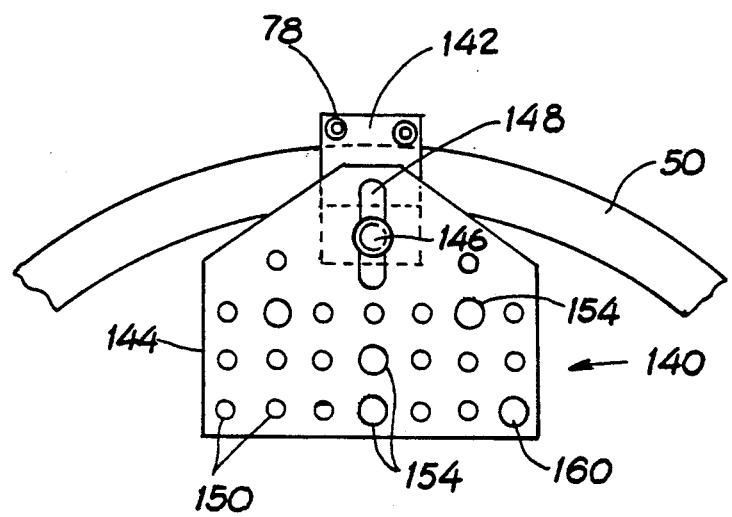
FIG. 10 is an isolated elevational view of the calibration frame mounted on at least one brace of the invention.
Figure 11:
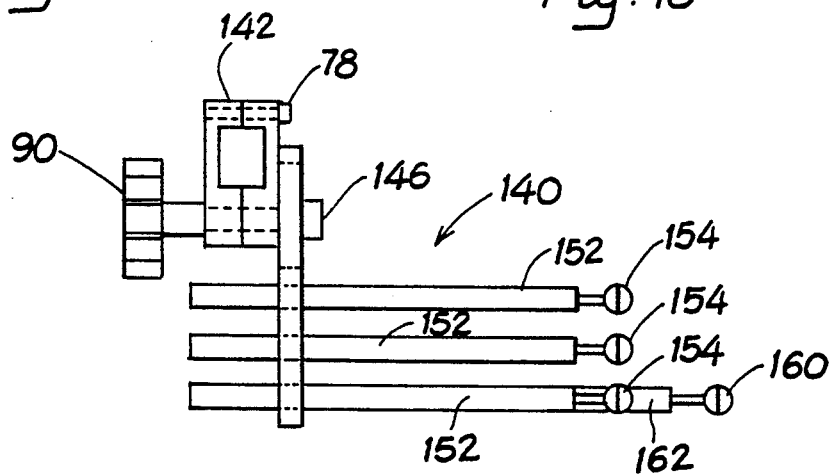
FIG. 11 is an isolated view of the calibration frame shown in FIG. 10, not including the brace of the invention, as seen from the left side of that figure.

In order to complete the procedure just described, it is also necessary to have a reference system that permits the exact positioning of the table 20 within the calibration system of the radiographic and linac apparatus. For that purpose, the body-support frame 200 also comprises at least one radiographic calibration device 140 mounted on one brace 50, as illustrated in FIGS. 10 and 11. Although not critical, greater flexibility is achieved if each brace includes a calibration device because the more convenient one can then be used, as determined by the position of the table in the radiographic imaging machine. The device 140 comprises a bracket 142 (which may be identical to the vise 72 of the skeletal fixation mechanism) adjustably fastened to the brace 50 and supporting a flat panel 144 mounted perpendicularly to the main axis of the table 20. The panel is mounted on the bracket by means of a bolt 146 in an elongated slot 148 that permits the adjustment of the panel to different elevations and angles with respect to the brace. If necessary, the bracket can also be moved along the span of the brace so that the panel can be positioned as desired within the cross-section of the table. A plurality of longitudinal support holes 150 is provided in the panel 144 that can be used to firmly hold calibration rods 152 in parallel to the main axis of the table (that is, the x coordinate). As seen in FIG. 11, each of these rods inserted into a support hole 150 includes a radiographically discernible target 154 at the tip. The purpose of these rods and targets is to enable the user to set a fixed reference plane, defined by the position of three targets 154, perpendicularly to the main axis of the table. This reference plane is first used for aligning the table with the radiographic equipment and for calculating the coordinates of the region of interest with reference to that plane. Then the plane defined by the three targets 154 is used to align the table with the reference system of the linac equipment, so that the calculated coordinates may be used to focus the radiation beam on the region of interest for stereotactic treatment. Note that the patient is kept immobilized on the table during the entire procedure by the two skeletal fixation mechanisms mounted on the braces of the invention.

In the preferred embodiment, the calibration rods 152 are made of phenolic material, which produces negligible artifacts in radiographic images and, because manufactured by the consistent-diameter centerless-ground process, can be made with a very precise constant diameter; each target 154 consists of a painted lucite ball approximately 1.3 cm in diameter, which produces a visible artifact, and a smaller, concentric steel ball about 4 mm in diameter, which is contained within the lucite ball and produces a clearly visible image; and each lucite ball contains a fine circumferential calibration line perpendicular to the main axis of the rod (that is, along the y-z plane equator the ball). This line permits the use of external sighting with an orthogonal laser system, such as is available in radiographic-imaging and radiation-treatment equipment, to define very accurately a reference plane perpendicular to the table. Once the table with an immobilized patient is introduced into the radiographic imaging machine, the machine's orthogonal laser sighting system is activated and three targets 154 are aligned with the plane defined by the laser by sliding the calibration rods 152 attached to the balls within their support holes 150 until the equator of each ball is perfectly lined up with the laser plane. Obviously, the three parallel rods must be mounted on support holes 150 that do not result in the rods being coplanar, inasmuch as the three selected targets can define a plane only if they are not in a straight line within the laser plane (which would necessarily be the case if the rods lied on the same plane). The calibration rods 152 are then locked in place by apposite locking screws (not shown in the figures) in the panel 144. In another embodiment, the rods 152 are threadably mounted on the panel, so that the position of each target 154 is adjusted by rotating the corresponding rod with respect to the panel and then fixed by a locking nut, as would be obvious to one skilled in the art.

Figure 12:
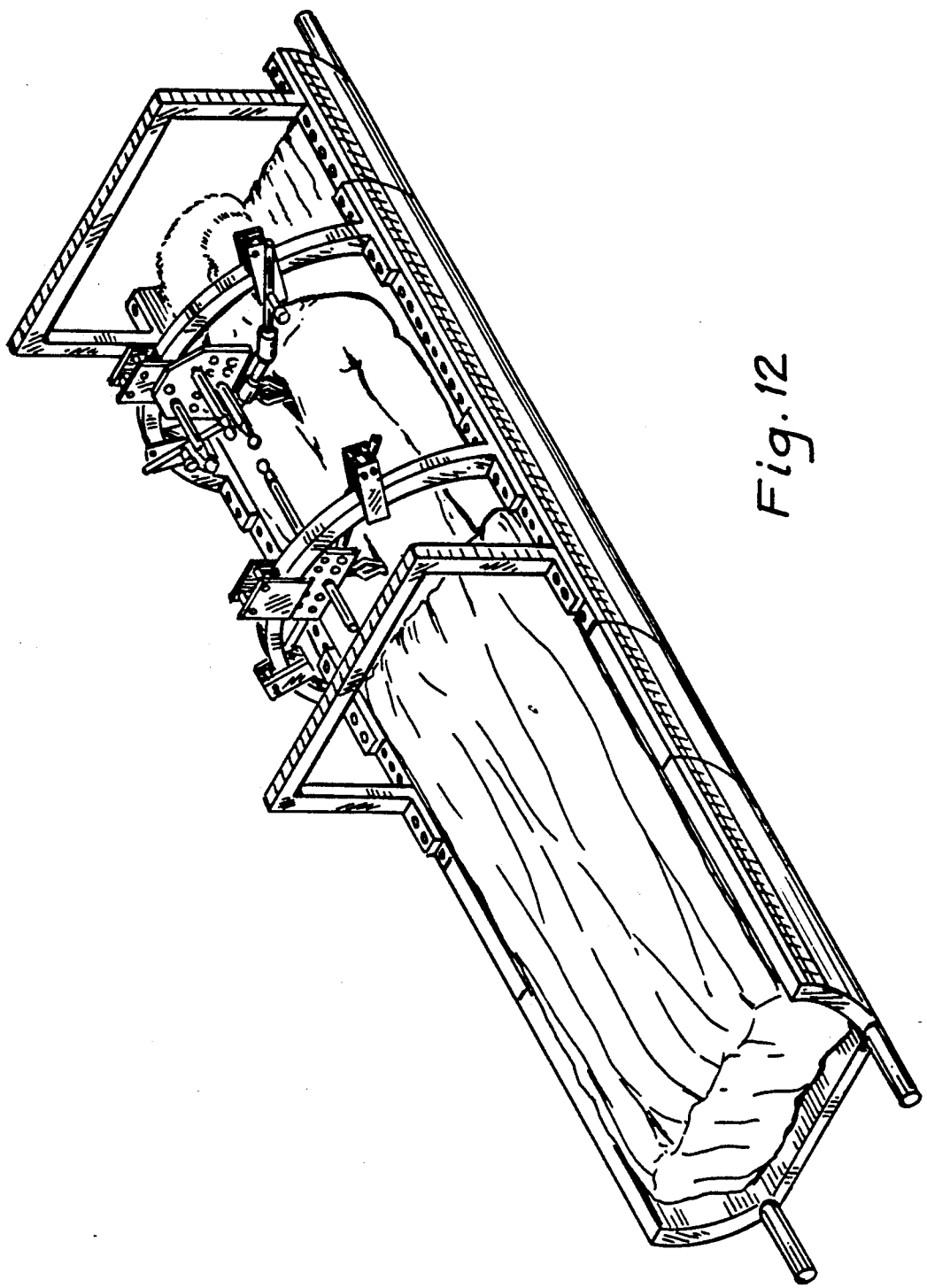
FIG. 12 is a perspective view of the preferred embodiment of the invention containing a patient immobilized within the body-support frame as it would appear during use.

The most critical feature of this invention is the ability to pinpoint the exact location of a tumor and to provide a system of reference through which the tumor can then be targeted exactly in a radiation machine. The usefulness of the invention is measured by the margin of error within which this can be achieved, which must be within the tolerances acceptable for a given procedure. Thus, in order to further refine the accuracy of the invention, an additional radiographic target 160 is provided that permits the translation of the coordinates of the tumor to a reference system as close as possible to the tumor itself. The target 160 is essentially the same as the three targets 154 used to define the reference plane discussed above, but it is used instead to choose and fix an additional reference point as close as possible to the tumor. The positioning rod 162 to which the target 160 is affixed is slided in an appropriate support hole 150 and the panel 144 is positioned so that the target 160 can be set at a point near the tumor on the body of the patient. FIG. 12 illustrates a patient lying face-down on the table of the invention and immobilized by two skeletal fixation clamps that grip spinous processes chosen above and below the tumor, so as to provide skeletal fixation immediately adjacent to the area of interest. Three calibration targets 154 have been aligned to lie on a plane of known position orthogonal to the table, and the radiographic target 160 is positioned close to the tumor in the patient.

In operation, the body-support frame of this invention is used as follows. The support panel 40 is slided along its tracks to a position corresponding to the region of interest in a patient lying on the table, so that cross-sectional radiographic scan images of the tumor area will encompass a sectional view of the N-shaped reference sight 32. The patient is then positioned on the table and the two braces 50 are moved along the retaining side-walls 24 to encompass the tumor and a chosen skeletal structure anatomically associated with the tumor. Using a chordoma as an example, the spinal column would be selected to immobilize the patient. Then, two surgical incisions are made caudad and craniad to the tumor to gain access to the parts of the bone to be clamped, such as the spinous process of two vertebrae, and the clamps 76 are positioned and fastened around the bone to provide a fixed connection, thus immobilizing the relevant part of the patient's body. At this point, the two braces 50 and all movable components of the skeletal fixation mechanisms 70 are tightened to provide a rigid frame holding the region of interest for stereotactic treatment in place.

The table is then introduced into the bore of a radiographic imaging machine and the three calibration targets 154 are visually aligned with the orthogonal laser sighting system of the machine in order to define a plane of reference in the table for use in determining the coordinates of the tumor. Since scanning equipment provides cross-sectional images taken at known distances in the x direction from the reference plane, the coordinates of each point in the region of interest can be calculated from the series of images of the tumor taken scanning the patient along the longitude of the table (x axis). At the same time, the distances separating the three rods of the N-shaped reference sight 32 in each scan image provide a check of the accuracy of the reported position of the scanning beam. If these distances in the images do not match the physical distances measured between the rods at a position corresponding to the x coordinate of the image, the scanning equipment is not properly calibrated with respect to the reference plane and an indication is given that appropriate adjustments need to be made.

Once the coordinates of the tumor in relation to the reference plane are established, the table is moved to the linear accelerator and the three calibration targets 154 are visually aligned with the orthogonal laser sighting system of the machine, so that the reference systems of the table and the machine coincide. If particularly great accuracy is required, such as in the of less than 1 mm, the radiographic target 160 is placed as near the tumor as practicable in a visible spot above the patient and the machine's laser sighting system is used again to determine the radiographic target's position with respect to the reference plane. This information permits the calculation of the coordinates of the tumor in relation to the radiographic target 160, which can now be used as a new reference point in the linac machine. Because of its relative closeness to the tumor, the radiographic target 160 makes it possible to minimize error in focussing the radiation beam on the tumor, thus increasing the accuracy of the stereotactic treatment. The operation of the frame of the invention is not described in great detail, other than as given above for purposes of illustration, because it is well understood by those skilled in the art of stereotactic surgery.

Thus, this invention provides a means for expanding radiosurgery outside the skull. The delivery of high-dose radiation in a single setting to radio-sensitive targets in the thorax, abdomen, paraspinal tissues, and extremities, which cannot be adequately treated with traditional radiation techniques, becomes possible with significant sparing of adjacent normal tissues.

Various other changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A body-support frame for skeletal fixation and stereotactic radiosurgery, comprising the following components:
   (a) first, rigid means for supporting a patient in a horizontal position;
   (b) second, rigid means, adjustably attached to said first means, for immobilizing by skeletal fixation a portion of the body of the patient targeted for stereotactic irradiation;
   (c) third means for defining a reference plane along the main axis of said first means; and
   (d) fourth means, rigidly attached to said first means, for measuring the coordinates of a region of interest with respect to the reference plane;
   wherein said second, rigid means for immobilizing by skeletal fixation the portion of the body of the patient targeted for stereotactic irradiation comprises two braces straddling said first means and sufficiently large to envelop the body of the patient, each of said braces lying in a plane orthogonal to the longitudinal axis of and being adjustably connected to said first means, so that the position of each brace can be shifted along the longitudinal axis of said first means to lie outside the region of interest in the patient;
   wherein said second, rigid means further comprises at least one vise slidably fastened to each of said braces, at least one swivel arm adjustably connected to said vise through an upper swivel joint, and a skeletal fixation clamp adjustably connected to said swivel arm through a lower swivel joint, so that the fixation clamp can be oriented to reach any point in the proximity of the brace across the width of the body-support frame; and
   wherein each of said two braces comprises two ends adjustably fastened to said first rigid means by removably pins that are slotted through said ends and into apposite receiving holes located at exact discrete intervals along said first means.

2. A body-support frame for skeletal fixation and stereotactic radiosurgery, comprising the following components:
   (a) first, rigid means for supporting a patient in a horizontal position;
   (b) second, rigid means, adjustably attached to said first means, for immobilizing by skeletal fixation a portion of the body of the patient targeted for stereotactic irradiation;
   (c) third means for defining a vertical reference plane perpendicular to a main axis of said first means, said third means being adjustable with respect to the position of said second means and along the main axis of the first means; and
   (d) fourth means, rigidly attached to said first means, for measuring the coordinates of a region of interest with respect to the reference plane.

3. The frame described in claim 2, wherein said first rigid means for supporting a patient in a horizontal position consists of a horizontal table comprising a flat horizontal platform, sufficiently long and wide to receive the body of a human patient, and of two retaining side-walls rigidly attached to the platform, so as to form a structure functionally equivalent to a conventional stretcher.

4. The frame described in claim 3, wherein said retaining side-walls are constructed in removable sections.

5. The frame described in claim 3, further comprising handles at each end of said table to permit the transportation of the patient held in the frame.

6. The frame described in claim 2, wherein the overall cross-sectional size of the body-support frame is capable of being fitted with an area corresponding to a circle approximately 28 inches in diameter.

7. The frame described in claim 2, wherein said second, rigid means for immobilizing by skeletal fixation the portion of the body of the patient targeted for stereotactic irradiation comprises two braces straddling said first means and sufficiently large to envelop the body of the patient, each of said braces lying in a plane orthogonal to the longitudinal axis of and being adjustably connected to said first means, so that the position of each brace can be shifted along the longitudinal axis of said first means to lie outside the region of interest in the patient.

8. The frame described in claim 7, wherein each of said two braces comprises two ends adjustably fastened to said first rigid means by removable pins that are slotted through said ends and into apposite receiving holes located at exact discrete intervals along said first means.

9. The frame described in claim 8, wherein said braces are arcuated and said second, rigid means for immobilizing by skeletal fixation the portion of the body of the patient targeted for stereotactic irradiation further comprises:
   two vises having opposite sides mounted on each brace;
   at least one tightening bolt connecting said opposite sides of each vise to fasten the vise to the desired position along the brace;
   a swivel rod rotatably mounted in a longitudinal bore between said two opposite sides of each vise, wherein said rod has a first end and a second end, and said first end contains a radial through-hole;
   a swivel arm having a cross-section conforming with said radial through-hole and being slidably connected therethrough to said swivel rod in each vise;
   a tightening knob screwably mounted on said second end of the rod of each vise to lock the rod in position by providing a clamping action between the knob and said swivel arm;

a double-swivel joint coupled to said swivel arm of each vise; and a skeletal fixation clamp coupled to said double-swivel joint connected to said swivel arm of each vise.

10. The frame described in claim 9, further comprising a tubular collar inserted around said swivel rod of each vise as a spacer to adjust the longitudinal position of the swivel arm.

11. The frame described in claim 9, wherein said skeletal fixation clamp consists of:
a support housing having two side-arms connected to said double-swivel joints coupled to the swivel arm of each vise, said support housing having a removable top that is clamped to the housing by means of at least one retaining screw and said support housing and removable top containing facing semicircular recesses that define a cylindrical channel disposed radially across the housing;
a clamp axle rotatably mounted in said channel; and
a skeletal fixation clamp rigidly attached to said clamp axle.

12. The frame described in claim 11, wherein said skeletal fixation clamp consists of two facing jaws each having transverse guide-holes; a threaded bolt passed through said transverse guide-holes in the jaws and screwably connected to a threaded nut; and a spring around the bolt between the two jaws of the clamp to urge the jaws to an open position.

13. The frame described in claim 12, wherein each of said jaws is approximately 5 cm long, 1.5 cm wide and 3 to 5 mm thick.

14. The frame described in claim 11, further comprising friction bumps on said jaws to increase their gripping ability.

15. The frame described in claim 11, wherein said skeletal fixation clamp consists of a cancellous screw mounted in said cylindrical channel of said support housing.

16. The frame described in claim 11, wherein said double-swivel joint consists of two facing blocks, each containing opposite hemispherical recesses wherein conforming spheres are rotatably housed, and a locking screw that fastens said two blocks together and provides tightening means around said spheres.

17. The frame described in claim 2, wherein said third means for defining a vertical reference plane perpendicular to a main axis of said first means consists of:
a bracket adjustably fastened to said second means;
a flat panel slidably mounted on said bracket perpendicularly to the main axis of the body-support frame;
a plurality of longitudinal support holes in said flat panel;
at least three calibration rods slidably held in said longitudinal support holes in parallel to the main axis of the body-support frame; and
a radiographically discernible target attached to each of said calibration rods.

18. The frame described in claim 17, wherein said calibration rods are made of phenolic material and each radiographically discernible target consists of a painted lucite ball approximately 1.3 cm in diameter containing a concentric steel ball about 4 mm in diameter; and wherein each lucite ball contains a fine circumferential calibration line perpendicular to the main axis of the rod.

19. The frame described in claim 2, wherein said fourth means for measuring the coordinates of a region of interest with respect to the reference plane consists of three measurement scales affixed to said first means in positions corresponding to a selected system of coordinates.

20. The frame described in claim 19, wherein said selected system of coordinates is the orthogonal x,y,z coordinate system.

21. The frame described in claim 2, further comprising an N-shaped reference sight slideably positioned on horizontal supporting tracks on said first means for radiographic confirmation of the exact position of scanner images taken along the longitudinal axis of the body-support frame.

22. The frame described in claim 21, wherein said N-shaped reference sight consists of three straight segments of aluminum, wherein two segments corresponding to the parallel legs of the N-shaped sight are placed precisely in parallel to the main axis of the body-support frame and the slanted segment is disposed across the width of the frame in variable x-y coordinates.

23. The frame described in claim 22, wherein said N-shaped reference sight is attached to a rigid support panel slidably mounted on supporting longitudinal tracks, so that the sight can be moved along the main axis of the frame to a position underlying the region of interest in the body of a patient lying in said first means, and so that the sight is visible in radiographic images produced in scanning the region.

24. The frame described in claim 2, further comprising a radiographic target capable of being positioned in close proximity to the region of interest for stereotactic radiosurgery.

25. The frame described in claim 24, wherein said radiographic target consists of:
a bracket adjustably fastened to said second means;
a flat panel slidably mounted on said bracket perpendicularly to the main axis of the body-support frame;
a longitudinal support hole in said flat panel;
a positioning rod slidably held in said longitudinal support hole in parallel to the main axis of the body-support frame; and
a radiographically discernible target attached to said positioning rod.

26. The frame described in claim 25, wherein said positioning rod is made of phenolic material and said radiographically discernible target consists of a painted lucite ball approximately 1.3 cm in diameter containing a concentric steel ball about 4 mm in diameter; and wherein each lucite ball contains a fine circumferential calibration line perpendicular to the main axis of the rod.

27. A body-support frame for skeletal fixation and stereotactic radiosurgery, comprising the following components:
(a) a horizontal table comprising a flat horizontal platform, sufficiently long and wide to receive the body of a human patient, and two removable, multiple-section retaining side-walls rigidly attached to the platform, so as to form a structure functionally equivalent to a conventional stretcher;
(b) handles at each end of said table to permit the transportation of the patient held in the frame;
(c) two braces straddling said horizontal table and sufficiently large to envelop the body of the patient, each of said braces lying in a plane orthogonal to the longitudinal axis of said platform and being adjustably connected to said side-walls, so that the position of each brace can be shifted along the longitudinal axis of said platform to lie outside the region of interest in the patient;

(d) at least one vise slidably fastened to each of said braces, at least one swivel arm adjustably connected to said vise through an upper swivel joint, and a skeletal fixation clamp adjustably connected to said swivel arm through a lower swivel joint, so that the fixation clamp can be oriented to reach any point in the proximity of the brace across the width of the body-support frame;

(e) a bracket adjustably fastened to said brace;

(f) a flat panel slidably mounted on said bracket perpendicularly to the main axis of the body-support frame;

(g) a plurality of longitudinal support holes in said flat panel;

(h) at least three calibration rods slidably held in said longitudinal support holes in parallel to the main axis of the body-support frame;

(i) a radiographically discernible target attached to each of said calibration rods;

(j) a positioning rod slidably held in one of said longitudinal support holes in parallel to the main axis of the body-support frame;

(k) a radiographically discernible target attached to said positioning rod;

(l) three measurement scales affixed to said horizontal table in positions corresponding to an orthogonal x,y,z coordinate system; and (m) an N-shaped reference sight slidably positioned horizontally on said platform for radiographic confirmation of the exact position of scanner images taken along the longitudinal axis of the body-support frame.

* * * * *